(12) United States Patent
van den Berg

(10) Patent No.: US 9,352,037 B2
(45) Date of Patent: May 31, 2016

(54) COMPOSITIONS AND METHODS TO ENHANCE THE IMMUNE SYSTEM

(71) Applicant: Timo Kars van den Berg, Amsterdam (NL)

(72) Inventor: Timo Kars van den Berg, Amsterdam (NL)

(73) Assignee: STICHTING SANQUIN BLOEDVOORZIENING, Amsterdam (NL)

(*) Notice: Subject to any disclaimer, the term of this patent is extended or adjusted under 35 U.S.C. 154(b) by 0 days.

(21) Appl. No.: 14/153,714

(22) Filed: Jan. 13, 2014

(65) Prior Publication Data

US 2014/0199308 A1 Jul. 17, 2014

Related U.S. Application Data

(62) Division of application No. 12/937,764, filed as application No. PCT/NL2009/050220 on Apr. 23, 2009, now Pat. No. 8,728,476.

(30) Foreign Application Priority Data

Apr. 23, 2008 (EP) .................... 08155011

(51) Int. Cl.
| | |
|---|---|
| A61K 39/395 | (2006.01) |
| A61K 39/275 | (2006.01) |
| C07K 16/30 | (2006.01) |
| A61K 39/12 | (2006.01) |
| C07K 16/28 | (2006.01) |
| A61K 39/00 | (2006.01) |

(52) U.S. Cl.
CPC ............ *A61K 39/3955* (2013.01); *A61K 39/12* (2013.01); *A61K 39/275* (2013.01); *A61K 39/395* (2013.01); *C07K 16/2803* (2013.01); *C07K 16/30* (2013.01); *A61K 2039/507* (2013.01); *A61K 2039/57* (2013.01); *C07K 2317/732* (2013.01); *C07K 2317/77* (2013.01); *C12N 2710/24034* (2013.01); *C12N 2710/24134* (2013.01)

(58) Field of Classification Search
None
See application file for complete search history.

(56) References Cited

U.S. PATENT DOCUMENTS

| | | | |
|---|---|---|---|
| 5,057,604 | A | 10/1991 | Brown |
| 6,972,324 | B2 | 12/2005 | Adolf et al. |
| 2003/0054415 | A1 | 3/2003 | Buhring et al. |
| 2004/0213792 | A1 | 10/2004 | Clemmons et al. |

FOREIGN PATENT DOCUMENTS

| | | |
|---|---|---|
| JP | 20078895 | 1/2007 |
| WO | 02092784 | 8/1999 |
| WO | 9940940 | 8/1999 |
| WO | 00/05268 | 2/2000 |
| WO | 0148020 A1 | 7/2001 |
| WO | 01/79299 A1 | 10/2001 |
| WO | 2006/089690 A1 | 8/2006 |
| WO | 2007133811 A2 | 11/2007 |
| WO | 2009091601 | 7/2009 |

OTHER PUBLICATIONS

Groner et al, Bioengineered, Dec. 2012, vol. 3, pp. 320-325.*
Robinson, PLoS Biology, 2004, vol. 1, pp. 0018-0020.*
Tibes et al (Cancer, 2006, vol. 106, pp. 2545-2651).*
Musolino et al (Journal of Clinical Oncology, vol. 26, pp. 1789-1796).*
Rudikoff et al. (Proc Natl Acad Sci USA 1982 vol. 79, pp. 1979-1983).
MacCallum et al. (Journal of Molecular Biology, 1996 vol. 262, pp. 732-745).
Casset et al. (Biochemical and Biophysical Research Communications, 2003 vol. 307, pp. 198-205).
Strome et al. (The Oncologist, Sep. 2007).
Oldenborg et al. (Science, Jun. 2000, vol. 288).
Melero et al. (Nature Reviews Cancer, Feb. 2007, vol. 7).
Olsson et al. (Blood, Jan. 2005, vol. 105(9)).
Kim et al. (Tumour Biol., May 2008, vol. 29(1)).
Oldenborg et al. (J Exp Med., Apr. 2001, vol. 193(7)).
McKenzie et al. (Curr Opin Hematol, Jan. 1998, vol. 5(1)).
Co et al. (Journal of Immunology, Feb. 1992, vol. 148).
Mori et al. (Cytotechnology, Oct. 2007, vol. 55).
Okazawa et al. (J Immunol., 2005, vol. 174).
Leonard et al. (J Clin Oncol., Jun. 2005, vol. 23(22)).
Leonard et al. (Annals of Oncology, Apr. 2007, vol. 18).
Damiano et al. (Proc Natl Acad Sci USA, Jul. 2007, vol. 104).
Kimura et al. (Cancer Sci., May 2007, vol. 98(8)).
Stroh et al. (Journal of clinical Oncology, 2010, vol. 28).
Lu et al. (J Natl Cancer Inst., Dec. 2001, vol. 93).
Notice of Opposition to a European Patent (EPO Form 2300E).
Third Party Observations for EP20090734943, submitted to the EPO on Mar. 3, 2016.
Summons to Attend Oral Proceedings, EPO, Mar. 29, 2016.

* cited by examiner

*Primary Examiner* — Karen Canella
(74) *Attorney, Agent, or Firm* — Hoffmann & Baron, LLP

(57) ABSTRACT

The invention relates to the field of molecular medicine. In particular, it relates to compositions and methods to enhance the clearance of aberrant cells, e.g. cancer cells or virus-infected cells, by the host's immune system. Provided is a composition comprising (i) a therapeutic compound that can trigger a host's immune effector cells against an aberrant cell, such as a therapeutic antibody, and (ii) at least one agent capable of reducing or preventing inhibitory signal transduction initiated via SIRPalpha.

2 Claims, 5 Drawing Sheets

COMPOSITIONS AND METHODS TO ENHANCE THE IMMUNE SYSTEM

Figure 1:
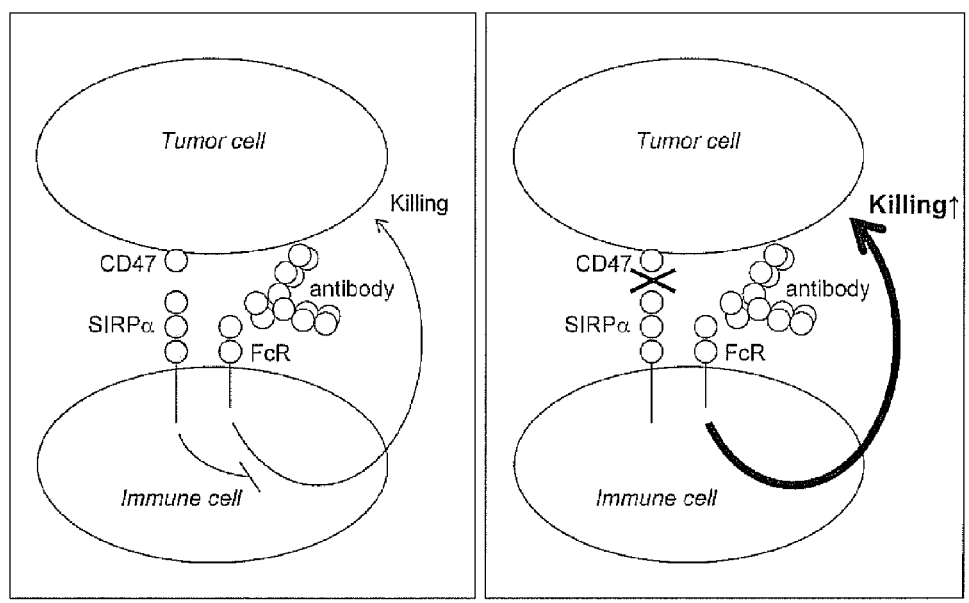

This application is a divisional of U.S. patent application Ser. No. 12/937,764 filed Nov. 2, 2010, which claims priority to International Application Number PCT/NL2009/050220 filed 23 Apr. 2009 and European Patent Application Number 08155011.3 filed 23 Apr. 2008, each of which are incorporated herein by reference.

The invention relates to the field of molecular medicine. In particular, it relates to compositions and methods to enhance the clearance of aberrant cells, e.g. cancer cells or virus-infected cells, by the host's immune system. Among others, it provides an enhanced efficiency of the treatment of human subjects with a therapeutic antibody, in particularly through an increase in antibody-dependent cell mediated cytotoxicity (ADCC).

The immune system defends the body against infection, disease and foreign substances. It is made up of many organs and cells. An antigen is a substance that causes the immune system to make a specific response, called the immune response. Viruses, bacteria, germs, and parasites contain substances that are not normally present in the body and thus cause an immune response. The immune response can lead to destruction of the antigen and anything it is part of or to which it is attached. Several different types of cells are involved in the immune system's response to an antigen. Among the cells are macrophages, granulocytes, dendritic cells, natural killer cells and lymphocytes. Among the lymphocytes cells are B cells (B lymphocytes), T cells (T lymphocytes), Killer T cells, and Helper T cells.

Cancer cells have substances on their outer surfaces that can act as antigens and thus "mark" the cells as different or abnormal. Viruses, bacteria, and parasites have components that are substantially different from normal human cells because they are truly foreign to the body and are detected by the immune system. However, the differences between cancer cells and normal human cells may be more difficult for the immune system to detect. Cancer immunotherapies, typically employing monoclonal antibodies, are designed to help the immune system to recognize cancer cells and/or to strengthen the immune response to the cancer cells and thus destroy the cancer.

Various therapeutic strategies in human beings are based on the use of therapeutic antibodies. This includes, for instance, the use of therapeutic antibodies developed to deplete target cells, particularly diseased cells such as virally-infected cells, tumor cells or other pathogenic cells. Such antibodies are typically monoclonal antibodies, of IgG species, typically with human IgG1 or IgG3 Fc portion. These antibodies can be native or recombinant antibodies, humanized mice antibodies (i. e. comprising functional domains from various species, typically Fc portion of human or non human primate origin, and variable region or complementary determining region (CDR) of mice origin). Alternatively, the monoclonal antibody can be fully human through immunization in human Ig locus transgenic mice or obtained through cDNA libraries derived from human cells. A particular example of such therapeutic antibodies is rituximab (Mabthera™; Rituxana), which is a chimeric anti-CD20 monoclonal antibody made with human γ1 and κ constant regions (therefore with human IgG1 Fc portion) linked to murine variable domains conferring CD20 specificity. In the past few years, rituximab has considerably modified the therapeutical strategy against B lymphoproliferative malignancies, particularly non-Hodgkin's lymphomas (NHL). Other examples of humanized IgG1 antibodies include alemtuzumab (Campath™, which is used in the treatment of B cell malignancies or trastuzumab (Herceptin™), which is used in the treatment of breast cancer.

Therapeutic antibodies achieve their therapeutic effect through various mechanisms. They can have direct effects in producing apoptosis or programmed cell death in e.g. tumor cells. They can block growth factor receptors, effectively arresting proliferation of tumor cells.

Indirect effects include recruiting cells that have cytotoxicity, such as monocytes and macrophages. This type of antibody-mediated cell kill is called antibody-dependent cell mediated cytotoxicity (ADCC). Monoclonal antibodies can also bind complement, leading to direct cell toxicity, known as complement dependent cytotoxicity (CDC).

While therapeutic antibodies represent a novel specific and efficient approach to human therapy, particularly for treatment of tumors, they do not always exhibit a strong efficacy. For instance, while rituximab, alone or in combination with chemotherapy was shown to be effective in the treatment of both low-intermediate and high-grade NHL, 30% to 50% of patients with low grade NHL have no clinical response to rituximab. It has been suggested that the level of CD20 expression on lymphoma cells, the presence of high tumor burden at the time of treatment or low serum rituximab concentrations may explain the lack of efficacy of rituximab in some patients. Nevertheless, the actual causes of treatment failure remain largely unknown. There is therefore a need in the art for increasing the efficiency of the therapeutic antibodies.

Also, given the numbers of antibodies that have been tested in cancer indications, one might have predicted that anticancer antibodies would comprise the vast majority of agents on the list of FDA approved drugs. However, only 4 out of the 12 antibody therapeutics on this list are targeted for cancer therapy, and this appears largely due to the lack of patient benefit. Interestingly, it is now becoming clear that one of the main reasons for this is that cancer cells (like their healthy counterparts) are relatively resistant to immune-mediated killing mechanisms. The mechanism for this apparent resistance of cancer cells against host immunity has not been established.

A goal of the present invention is therefore to identify means and methods to enhance immunity and immunotherapy against aberrant cells, for example cancer cells. In particular, it is a goal to enhance the in vivo efficacy of a therapeutic compound that can trigger a host's immune effector cells against an aberrant cell.

Figure 2:
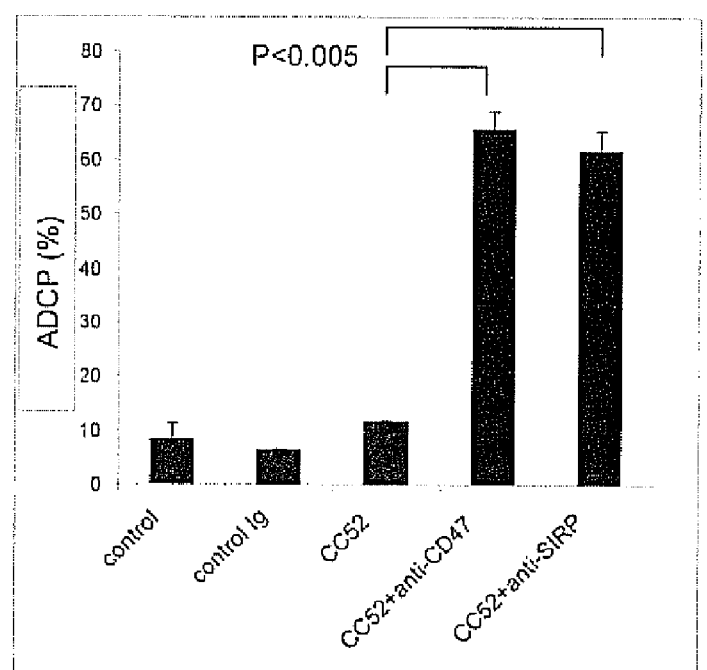
Figure 3:
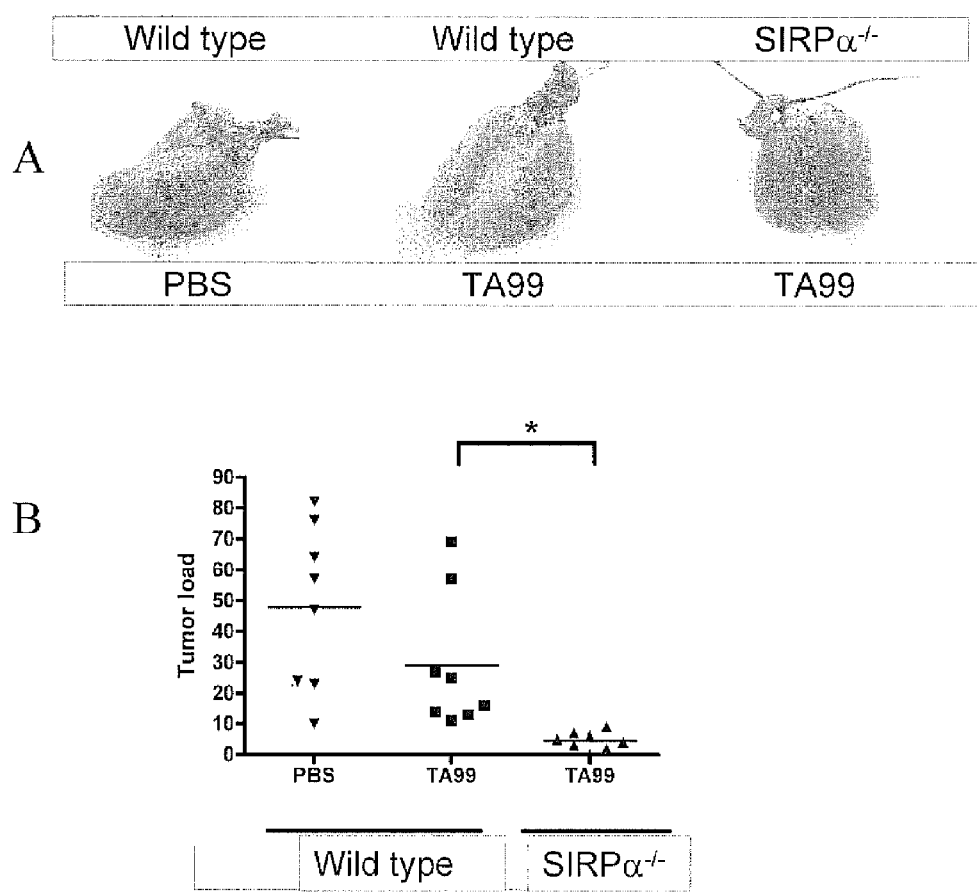

Interestingly, the present inventors discovered an endogenous mechanism that limits the killing of aberrant cells, e.g. cancer cells, by immune effector cells (see FIG. 1). This mechanism involves the molecular interaction between CD47, which is present on the surface of essentially all cells within the body of the host including cancer cells, and SIRPα, which is specifically expressed on immune cells, in particular on macrophages and granulocytes (Adams et al., 1998. J. Immunol. 161:1853-18592). Importantly, blocking the interaction between CD47 and SIRPα with antagonistic antibodies against either of the two components was found to dramatically enhance the in vitro killing of cancer cells in the presence of anti-cancer cell antibodies (FIG. 2). This effect was confirmed in a murine lung tumour model in SIRPα-mutant mice (FIG. 3). These data show that the binding of CD47 to SIRPα generates an inhibitory signal that suppresses ADCC by the immune system. Without wishing to be bound by theory, it is hypothesized that interference with the inhibitory signal via SIRPα leads to an enhanced activity of immune effector cells against an aberrant cells, presumably via an increase of the ADCC mechanism.

One aspect of the invention therefore relates to a composition comprising (i) a therapeutic compound that can trigger a host's immune effector cells against an aberrant cell and (ii) at least one agent capable of reducing or preventing inhibitory signal transduction initiated via SIRPα. For example, an agent is used which is capable of inhibiting the interaction between SIRPα and CD47, such that the inhibitory signal via the CD47-SIRPα interaction is reduced. A host is a mammal, preferably a primate or rodent, more preferably a human subject.

The therapeutic compound is a therapeutic antibody, in particular an antibody that induces or promotes antibody-dependent cellular cytotoxicity (ADCC). As used herein, ADCC is meant to encompass antibody-dependent cellular phagocytosis (ADCP) as well. Said therapeutic antibody is capable of forming an immune complex. In one embodiment, the therapeutic antibody has a human or non-human primate IgG Fc portion. Preferably, the therapeutic antibody is a monoclonal antibody or a functional fragment or a derivative thereof, more preferably a humanized, human or chimeric antibody. Said fragment or a derivative thereof is preferably selected from a Fab fragment, a F(ab')2 fragment, a CDR and a scFv. In a particular embodiment, the therapeutic antibody is an FDA approved therapeutic antibody, such as rituximab, herceptin, trastuzumab, alemtuzumab, bevacizumab, cetuximab or panitumumab. See for example Strome et al., Oncologist 2007; 12; 1084-1095.

Figure 4:
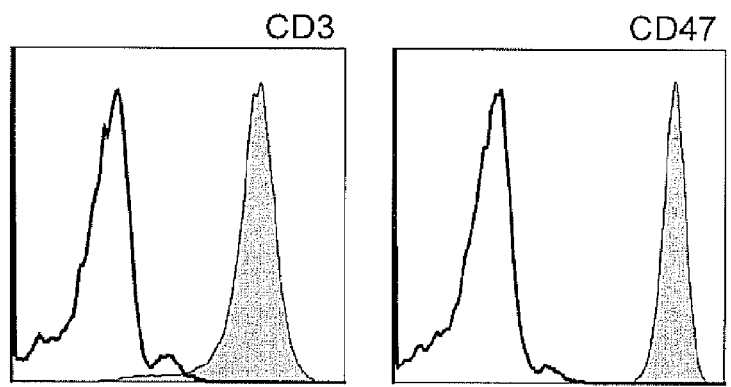
Figure 4:
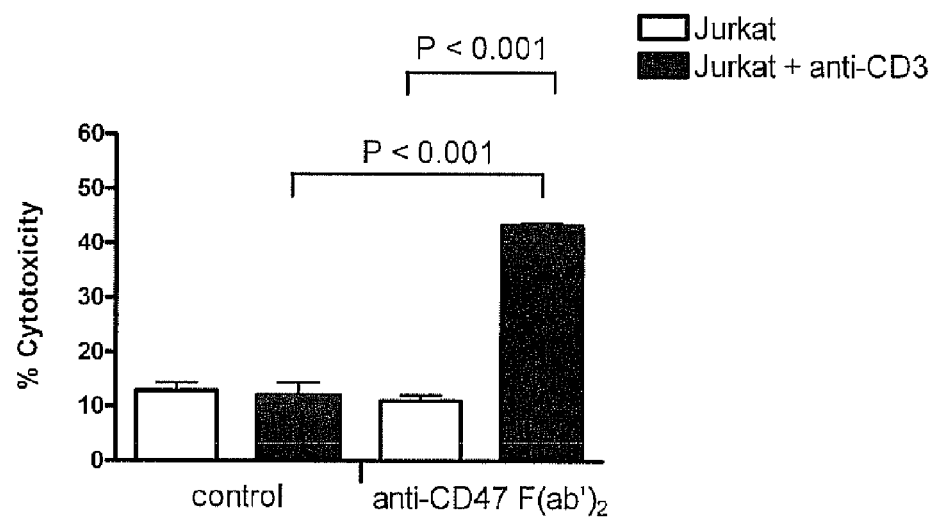

According to the invention, an agent capable of reducing or preventing inhibitory signal transduction initiated via SIRPa is used to partially or fully block the inhibitory signal via the CD47-SIRPα complex. Agents capable of reducing or preventing inhibitory signal transduction initiated via SIRPα, e.g. by inhibiting the interaction between SIRPα and CD47, are known in the art and further agents can be identified using known techniques based on a read-out of downstream signalling events. For example, the interaction of cell-associated CD47 with SIRPα expressed on the surface of myeloid cells is known to cause SIRPα tyrosine phosphorylation and to promote the recruitment and/or activation of the tyrosine phosphatases SHP-1 and SHP-2 as well as a number of other signalling proteins to the cytoplasmic part of the SIRPa protein (Oldenborg P A et al. (2000) Science 288:2051-4, Oshima et al. (2002) FEBS letters 519:1-7). These components, and in particular SHP-1, and perhaps also SHP-2, are known to mediate the negative effects of SIRPα triggering with respect to various downstream effects, including the phagocytosis of antibody- or complement-coated red blood cells (Oldenborg P A et al. (2001) J Exp Med. 193:855-62), and are therefore anticipated to also mediate the inhibitory regulation of ADCC. Therapeutic agents inhibiting the CD47-SIRPα interaction will likewise also prevent the recruitment and/or activation of SHP-1, SHP-2 and/or some of the other indicated signalling molecules. A substance to reduce or prevent inhibitory signal transduction initiated via human CD47-SIRPα interactions during ADCC can be selected using a series of assays aimed to detect: i) reduction of CD47-SIRPα interactions in general (Liu et al. (2007) J Mol Biol. 365:680-93, Liu et al. (2004) J. Immunol. 172: 2578-85) (FIG. 4), ii) reduction of CD47-dependent tyrosine phosphorylation of SIRPα and/or SHP-1 recruitment to SIRPa and resultant activation of the SHP-1 tyrosine phosphatase activity (Oldenborg P A et al. (2000) Science 288: 2051-4), and/or iii) enhancement of ADCC using therapeutic antibodies (e.g. trastuzumab, rituximab) against tumor (Mimura K et al. (2007) Oncology. 72:172-80, Shimadoi S et al. (2007) Cancer Sci. 98:1368-72, Lefebvre M L et al. (2006) J Immunother. 29:388-97) or other cells (e.g. red blood cells).

WO99/40940 discloses ligands of CD47 and agents binding to said ligands, such as CD47 antibodies and SIRPα, for the treatment of inflammatory, autoimmune and allergic diseases, graft rejection and/or chronic lymphocytic leukaemia.

It has been reported that ligation of SIRPα with specific antibody Fab fragments can suppress the production of inflammatory mediators by macrophages (Van den Berg et al., J. Leukocyte Biol. 1999; pg. 16)

WO02/092784 is related to polynucleotides and polypeptides relating to the modulation of SIRPα-CD47 interactions.

Armant et al. disclose that anti-CD47 monoclonal antibodies selectively suppress IL-12 release by monocytes (J. Exp. Med. Vol. 190, 1999, pg. 1175-1181).

Van den Berg et al. report that activated macrophages are the major cause of tissue damage during inflammation in the CNS. Three antibodies were selected which bind to the rat SIRPa receptor (J. Neuroimmunology, Vol. 90, 1998, pg. 53).

U.S. 2003/0026803 discloses a method for the treatment of an autoimmune disease with macrophage involvement, comprising administering an agent which inhibits the interaction between CD47 and SIRPα. Also described therein are methods for identifying such agents.

However, the use of a CD47/SIRPα inhibitory agent as disclosed herein, namely to enhance a host's immune effector cells, has not been disclosed or suggested in the art.

An "agent" or "antagonist", as referred to herein, may be substantially any molecule or process which is capable of achieving the required function, namely of reducing or preventing the CD47/SIRPα induced suppression of the cytolytic and/or phagocytic response of immune effector cells (see FIG. 1). This function is suitably achieved by inhibiting or interfering with the CD47-SIRPα interaction. "Inhibiting" the CD47/SIRPα interaction means that the functional relationship between the two molecules is altered such as to reduce or eliminate the killing-suppressive effects on the macrophage by CD47. For example, the biological interaction between SIRPα and CD47 may be reduced or altered, thereby preventing inhibitory signalling induced through SIRPα. Alternatively, the inhibitory signalling through SIRPα may be prevented without actually affecting the interaction with CD47.

Inhibitory molecules of a variety of types are known in the art, and can be used as a basis for the design of agents in accordance with the present invention. One or more agents of the same or of a different type (e.g. small molecule and antibody) may be used. In one embodiment, a composition comprises a proteinaceous substance capable of inhibiting the interaction between SIRPα and CD47. For instance, it is a peptide, an antibody or antibody fragment. Peptides according to the present invention are usefully derived from SIRPα, CD47 or another polypeptide involved in the functional SIRPα-CD47 interaction. Preferably, the peptides are derived from the N-terminal V-type immunoglobulin domains in SIRPα or CD47 which are responsible for SIRPα-CD47 interaction.

Preferred agents are antibodies or antibody fragments, which may be readily prepared and tested as described below, using techniques known in the art. For example, a composition comprises as antagonist of the CD47/SIRPα-induced signalling an anti-CD47 antibody, an anti-SIRPα antibody, or a fragment thereof.

Suitable CD47/SIRPα inhibitory agents for use in the present invention can be selected using an (high throughput) in vitro assay involving co-incubation of tumor cells and macrophages in the presence of a therapeutic antibody against the tumor cells and testing the efficacy of candidate agents e.g. a panel of monoclonal antibodies against either CD47 or SIRPα, to enhance antibody-dependent killing. See also Example 1. For example, phagocytosis and cytolysis of cultured human breast cancer cells by human monocyte-derived macrophages (MDM) or myelomonocytic cell lines mediated by a therapeutic antibody can be established in the presence and absence of a candidate antagonist agent. Such assay systems known in the art. For example, purified monocytes can be cultured with GM-CSF, M-CSF, or no cytokine for five or six days. Antibody dependent cellular phagocytosis (ADCP) and cytolysis (ADCC) assays can be performed with the MDM and HER-2/neu positive target cells (SK-BR-3). ADCP can be measured by two-color fluorescence flow cytometry using PKH2 (green fluorescent dye) and phycoerythrin-conjugated (red) monoclonal antibodies (MoAb) against human CD14 and CD11b. ADCC can suitably be measured with established radioactive 51-Cr release assays, or by a commercial non-radioactive LDH detection kit. However, other methods may also be used.

As will be understood, the present invention is advantageously used to enhance the in vivo efficacy of a therapeutic compound that can trigger a host's immune effector cells against any type of aberrant cell. As used herein, "aberrant cell" refers to any diseased or otherwise unwanted cell in a host organism.

In one embodiment, it is a cancer cell. For example, it is a non-Hodgkin's lymphoma cell, a breast cancer cell, a chronic lymphocytic leukaemia cell or a colorectal cancer cell.

Clearly, the blocking of CD47-SIRPα interactions by suitable antagonists offers great promise for enhancing antibody-mediated destruction of cancer cells. Principally, the added value of resolving the limitations of antibody therapy against cancer can occur at at least three distinct levels:

1. By decreasing the threshold of cancer cell killing, the dosing and/or frequency of antibody treatment can be lowered, resulting in a significant reduction of costs. This is of relevance, since the production of antibody therapeutics, which are generally humanized recombinant proteins, is expensive.
2. The cure- and survival-rates can increase significantly by increasing the overall effectiveness of antibody therapy.
3. Increasing ADCC can have a dramatic effect on the range of antibody therapeutics that would be suitable for clinical application. Many antibody therapeutics that would otherwise not have beneficial effects, may in combination with CD47-SIRPα antagonists prove to be effective. In fact, a number of the antibody therapeutics that have thus far not demonstrated sufficient activity in trials should perhaps be reconsidered.

One of the strengths of the concept of the present invention resides in its broad applicability. In principle, it can be expected to potentiate the effects of any therapeutic antibody against cancer, in particular those that exert their effects, at least in part, by ADCC. Furthermore, therapeutic antibodies which have not shown any ADCC component in the absence of CD47-SIRPα interference, may be able to raise a beneficial ADCC response upon blocking of CD47-SIRPα interactions. As indicated before most of the FDA-approved therapeutic antibodies are of the human IgG1 subclass, which can in principle be expected to be efficient inducers of ADCC. Thus, the present invention can be practiced in combination with the majority of therapeutic antibodies.

One embodiment of the invention relates to the use of an agent capable of reducing or preventing inhibitory signal transduction initiated via SIRPa inhibiting the interaction between SIRPα and CD47, in the preparation of a medicament for the treatment or prophylaxis of a disease or disorder that would benefit from enhanced phagocytosis by macrophages. Exemplary diseases that would benefit from enhanced phagocytosis by macrophages include cancer, such as non-Hodgkin's lymphomal, breast cancer, chronic lymphocytic leukaemia or colorectal cancer.

In fact, the treatment or prophylaxis of any disease or disorder wherein aberrant or otherwise unwanted cells are involved can benefit from the use of an inhibitory agent as disclosed herein. In one aspect, said disease is a viral infection, in particular in infection caused by a member of the family Poxviridae. As will be understood, an inhibitory agent, or a combination of two or more different inhibitory agents, may be used in the manufacture of a medicament in combination with a further therapeutic compound. In a preferred embodiment, said further therapeutic compound can trigger a host's immune effector cells against an aberrant cell.

In one aspect, the invention relates to a method of increasing ADCC in a subject receiving anti-cancer treatment, said method comprises administering to said subject prior to, simultaneously, before or after the administration of an anti-cancer medicament an agent capable of reducing or preventing inhibitory signal transduction initiated via SIRPa in an amount of sufficient to increase ADCC. For example, said anti-cancer medicament is a therapeutic antibody which inhibits the interaction between SIRPα and CD47. The subject to be treated is for example a patient suffering from non-Hodgkin's lymphomal, breast cancer, chronic lymphocytic leukaemia or colorectal cancer.

In a related aspect, there is provided a method of increasing ADCC in a subject receiving therapeutic antibody treatment, said method comprises administering to said subject prior to, simultaneously, before or after the administration of said therapeutic antibody an agent capable of reducing or preventing inhibitory signal transduction initiated via SIRPa in an amount of sufficient to increase ADCC.

Also, the invention provides a method of increasing the efficiency of a therapeutic antibody treatment in a subject, said method comprises administering to said subject prior to, simultaneously, before or after the administration of said therapeutic antibody an agent capable of reducing or preventing inhibitory signal transduction initiated via SIRPα.

In another embodiment, the invention provides the use of an agent capable of reducing or preventing inhibitory signal transduction initiated via SIRPa for the treatment or prophylaxis of a viral infection. In general, any method that promotes the host immune system to respond more efficiently to the virus is likely to increase its natural and acquired (e.g. by vaccination) immunity against the virus. In a specific aspect, the invention provides the use of an agent capable of inhibiting the interaction between SIRPα and CD47 for the manufacture of a medicament for the treatment or prophylaxis of disease caused by pox virus. Poxviruses (members of the family Poxviridae) can infect as a family both vertebrate and invertebrate animals. The prototype of poxvirus family is vaccinia virus, which has been used as a successful vaccine to eradicate smallpox virus. Vaccinia virus is also used as an effective tool for foreign protein expression to elicit strong host immune response. The name of the family, Poxviridae, is a legacy of the original grouping of viruses associated with diseases that produced poxs in the skin. Modern viral classification is based on the shape and molecular features of viruses, and the smallpox virus remains as the most notable member of the family. The only other poxvirus known to specifically infect humans is the molluscum contagiosum virus (MCV). Although the World Health Organization (WHO) declared the virus officially eradicated in 1977, post Sep. 11, 2001 the American and UK governments have had increased concern over the use of smallpox or small pox like disease, in bio-terrorism.

It has been established that poxviruses encode a homologue of CD47, termed viral CD47 (vCD47). By interacting with SIRPa on immune effector cells, the present inventors hypothesize that vCD47, in addition to endogenous CD47, can provide negative signals that prevent killing and/or phagocytosis of poxvirus-infected cells. In one embodiment, the invention thus provides a composition comprising (i) a therapeutic compound that can trigger a host's immune effector cells against a virally-infected cell, such as a cell infected by the poxvirus, and (ii) at least one agent capable of reducing or preventing inhibitory signal transduction initiated via SIRPα. Suitable therapeutic compounds include viral vaccines, preferably a poxviral vaccine.

The invention accordingly also provides the use of an inhibitory agent to reduce or prevent inhibitory signal transduction initiated via SIRPalpha, for instance induced by vCD47-SIRPα interaction, to (i) increase the natural host resistance to infection with poxviral pathogens, (ii) to enhance the efficacy of vaccination against poxviral pathogens) and/or to (iii) enhance the effectiveness of vaccination with poxviral vectors, such as vaccinia.

LEGENDS TO THE FIGURES

FIG. 1. Model for the role of CD47 and SIRPα in limiting the antibody-dependent killing of tumor cells by the immune system and potentiation of tumor cell destruction by blocking CD47-SIRPα interactions. Antibodies directed against the tumor cells are recognized by immune cell Fc-receptors and this induces tumor cell killing. Under normal conditions (left panel) this antibody-induced killing is limited by the interaction of CD47 on the tumor cells with SIRPα on the immune cell, which generates an intracellular signal that negatively regulates the killing response. By blocking the interaction between CD47 and SIRPα (right panel) the antibody-induced killing of tumor cells is enhanced because it is relieved from this limitation.

FIG. 2: Blocking CD47-SIRPα interactions with antagonistic monoclonal antibodies enhances CC52 antibody-dependent cellular phagocytosis of rat CC531 colon carcinoma cells by rat NR8383 macrophages. CC531 tumor cells and NR8383 macrophages were incubated in culture plates with medium in the absence or presence of CC52 antibody against CC531 cells and/or blocking monoclonal antibodies against either CD47 or SIRPα. After 1.5 hours the percentage of ADCP was determined. For details, see Example 1.

FIG. 3: SIRPα-derived signals limit the killing of B16 tumor cells in vivo. CD47-expressing B16 melanoma cells were injected into control (i.e. Wild type) mice or into mice lacking the SIRPα cytoplasmic tail that mediates intracellular signaling in immune cells (i.e. SIRPα−/−). Groups of mice were treated every other day for 2 weeks with a suboptimal dose of therapeutic antibody TA99 directed against the gp75 tumor antigen present on the B16 cells. One week afterwards the animals were sacrificed and lung tumor load was quantified. Representative pictures (panel A) from the lungs of these mice show that there is essentially no tumor formation in the antibody-treated SIRPα−/− mutant mice as compared to the antibody-treated wild type mice, identifying a negative role of SIRPa signaling in tumor cell elimination in vivo. Each point in the graph (panel B) represents evaluation of a single animal. *, $p<0.005$, students T-test.

FIG. 4: ADCC of human monocytes towards Jurkat acute T leukemia cells is enhanced by blocking CD47-SIRPα interactions. (A) Surface expression of CD3 (using CLB-T3/4.2a mAb) and CD47 (using B6H12 mAb) and on Jurkat cells as evaluated by flow cytometry. (B) ADCC of human monocytes towards Jurkat cells after pre-incubation with mouse $IgG_{2a}$ anti-CD3 (20 μg/ml) and/or B6H12 (50 μg/ml) anti-CD47 $F(ab')_2$. Saturation of Jurkat cells with anti-CD47 $F(ab')_2$ was confirmed by parallel flow cytometric staining (data not shown). Note that virtually no killing is induced by anti-CD3 in absence of CD47-SIRPα blocking, whereas substantial levels of killing are evoked in the presence of anti-CD47 $F(ab')_2$. Values shown are means±SD (n=3) from a representative experiment out of three.

FIG. 5: Rituximab-mediated ADCC of human monocytes towards Raji Burkitt's B cell lymphoma cells is enhanced by blocking CD47-SIRPα interactions. (A) Surface expression of CD20 (using anti CD20 Rituximab) and CD47 (using anti-CD47 B6H12 mAb) and on Raji cells as evaluated by flow cytometry. Red histogram represents control and blue histogram represents the Rituximab (upper histogram) or CD47 staining (lower histogram) (B) ADCC of human monocytes towards Raji cells after pre-incubation with Rituximab (20 μg/ml) and/or B6H12 (10 μg/ml) anti-CD47. ADCC was performed at an effector:target ratio of 50:1. Note that the Rituximab-mediated killing of Raji cells is significantly enhanced by anti-CD47 mAb. Values shown are means±SD (n=3) from a representative experiment. * statistically significant difference, $p<0.05$.

The invention is exemplified by the following examples.

EXAMPLE 1

In Vitro Evidence for a Role of CD47-SIRPα Interactions in ADCC

In order to investigate the contribution of the CD47-SIRPα interaction during ADCC of tumor cells by macrophages an assay was employed in which CC531 rat colon carcinoma cells were incubated with CC52 antibody and rat NR8383 effector cell macrophages.

Materials and Methods:

Rat CC531 colon carcinoma cells and NR8383 rat alveolar macrophages were routinely cultured in RPMI-1640 medium containing 10% fetal calf serum (FCS) (Gibco BRL) and antibiotics. CC531 were detached from the tissue flasks by scraping, washed in PBS, and labelled with 5 μM of DiI (Molecular Probes) for 15' at RT. After washing $3.75\times10^5$ CC531 cells, either preincubated or not for 15' with 5 μg/ml anti-rat CD47 antibody OX101, were incubated, in a round-bottomed 96-well tissue culture plastic plate in 200 μl of HEPES-buffered RPMI-1640 containing 0.5% BSA, with $1.25\times10^5$ NR8383 cells, either preincubated or not for 15' with 5 μg/ml anti-rat SIRPa antibody ED9 or its Fab'-fragments, in the presence or absence of CC531-reactive mAb CC52 (1 μg/ml). After incubation for 90' at 37° C. the cells were washed and stained using the macrophage specific biotinylated antibody ED3 (directed against rat sialoadhesin) and FITC-labelled streptavidin. ADCP (expressed as the % of NR8383 having ingested DiI-labelled CC531 cells) was determined on a FACScan flow cytometer (Becton and Dickinson).

Results:

In the absence of blocking antibodies against CD47 (O×101) or SIRPα (ED9) only very little antibody-dependent cellular phagocytosis is observed, whereas in the presence of such antibodies CC531 are readily phagocytosed (FIG. 2). This shows that interactions between CD47-SIRPα on respectively tumor cells and macrophage effector cells can negatively regulate ADCC in vitro.

EXAMPLE 2

In Vivo Evidence for a Role of SIRPα Signalling in Antibody-Dependent Tumor Cell Killing In order to demonstrate that SIRPa provides signals that inhibit tumor cell killing in vivo we compared antibody-dependent tumor cell killing in wild type and SIRPα-mutant mice (Yamao (2002) J Biol Chem. 277:39833-9) using an in vivo B16F10 mouse melanoma model (Bevaart L et al. (2006) Cancer Res. 66:1261-4). The SIRPa mutant mice lack the complete cytoplasmic tail, including the ITIM motifs that act as docking sites for SHP-1 and SHP-2.

Materials and Methods:

Young adult (7 weeks old) C57B1/6 wild type or SIRPa-mutant mice (Yamao (2002) J Biol Chem. 277:39833-9) were injected i.v. $1.5 \times 10^5$ B16F10 melanoma cells (in 100 µL saline; obtained from the National Cancer Institute (Frederick, Md.), in the absence or presence of therapeutic antibody TA99 (10 µg/mouse at day 0, 2, 4, 7, 9, and 11 after tumor cell injection). After 21 days the animals were sacrificed and the number of metastases and tumor load in the lungs was determined as described (Bevaart L et al. (2006) Cancer Res. 66:1261-4).

Results:

As can be seen in FIG. 3 there was a significantly lower level of tumor development in the SIRPα-mutant mice as compared to wild type mice using suboptimal concentrations of therapeutic monoclonal antibody TA99. These results demonstrate that SIRPa is a negative regulator of tumor cell killing in vivo.

EXAMPLE 3

To provide further evidence for a negative role of CD47-SIRPα interactions in tumor cell killing by myeloid cells, we established an ADCC assay employing human CD47-expressing Jurkat T cell leukemic cells, opsonized with a murine $IgG_{2a}$ anti-CD3 antibody (Van Lier R A et al. Eur J Immunol. 1987; 17:1599-1604) as a target (FIG. 4A), and human SIRPα-expressing monocytes as effector cells, and used this to test the effect of antibodies that block CD47-SIRPα interactions.

ADCC Assay

Monocytes were isolated by magnetic cell sorting by using anti-CD14 coated beads according to the manufacturer's instructions (Miltenyi Biotec B. V., Utrecht, The Netherlands) from PBMC isolated by density centrifugation using isotonic Percoll (Pharmacia Uppsala, Sweden) from heparinized blood obtained from healthy volunteers. The cells were cultured for 16 h in complete RPMI supplemented with 5 ng/ml recombinant human GM-CSF (Pepro Tech Inc, USA), harvested by mild trypsin treatment, and washed. Jurkat cells ($5-8 \times 10^6$ cells) were collected and labeled with 100 µCi$^{51}$Cr (Perkin-Elmer, USA) in 1 ml for 90 min at 37° C. Where indicated the cells were preincubated with anti-CD47 and/or anti-CD3, and washed again. Monocytes were harvested and seeded in 9-well U-bottom tissue culture plates in RPMI with 10% FCS medium. The target cells ($5 \times 10^3$/well) and effector cells were co-cultured in 96-well U-bottom tissue culture plates in complete medium at a ratio of E:T=50:1 for 4 hours at 37° C., 5% $CO_2$. Aliquots of supernatant were harvested and analyzed for radioactivity in a gamma counter. The percent relative cytotoxicity was determined as [(experimental cpm−spontaneous cpm)/(Total cpm−spontaneous cpm)]×100%. All samples were tested in triplicate.

Results:

As can be seen in FIG. 4B. anti-CD3-mediated ADCC against Jurkat cells, which express high levels of surface CD47 (FIG. 4A), is potently and synergistically enhanced by saturating concentrations of F(ab')$_2$-fragments of the antibody B6H12 that blocks CD47 binding to SIRPα. Notably, in the absence of effector anti-CD3 antibody no effect of anti-CD47 F(ab')$_2$ was observed, suggesting that CD47-SIRPα interactions act selectively to restrict antibody- and Fc-receptor-mediated affects on tumor cell killing.

Collectively, these data demonstrate that CD47-SIRPα interactions, and the resultant intracellular signals generated via SIRPα in myeloid cells, form a barrier for antibody-mediated destruction of tumor cells. These results provide a rationale for employing antagonists of the CD47-SIRPα interaction in cancer patients, with the purpose of enhancing the clinical efficacy of cancer therapeutic antibodies.

EXAMPLE 4

Figure 5:
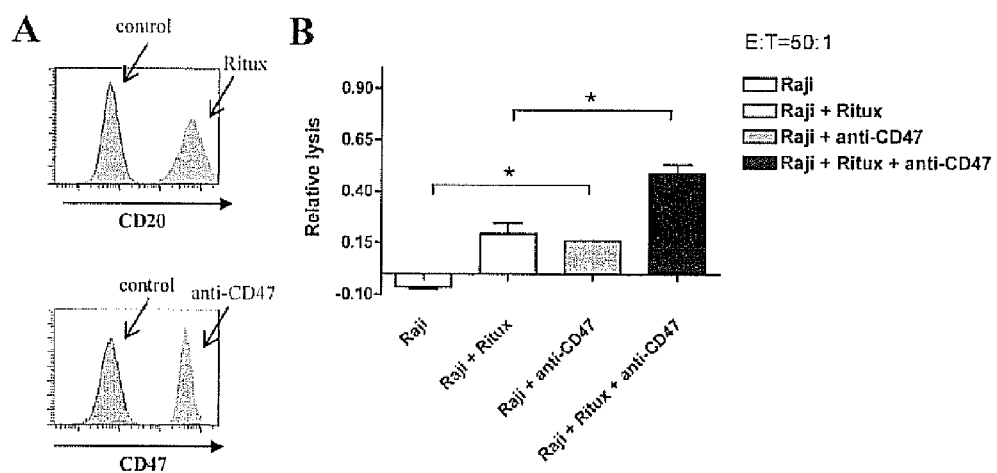

Blocking of CD47-SIRPα Interactions Enhances the Effect of Anti-Cancer Therapeutic Antibodies In order to demonstrate that the blocking of CD47-SIRPα interactions indeed enhance the effect of established anti-cancer therapeutic antibodies, we developed an ADCC assay using human Raji Burkitt's B lymphoma cells as targets, human monocytes as effector cells, and an FDA-approved therapeutic antibody against CD20 (Rituximab). For experimental details see the legend to FIG. 5. As can be seen in FIG. 5, the blocking antibody against CD47, B6H12, was able to significantly enhance the Rituximab-mediated cytotoxicity towards Raji cells.

The invention claimed is:

1. A composition comprising
   (i) a therapeutic compound that can trigger a host's immune effector cells against a cancer cell, wherein said therapeutic compound is a therapeutic antibody comprising a human or non-human primate IgG Fc portion, wherein the therapeutic antibody induces antibody-dependent cellular cytotoxicity (ADCC), and wherein the therapeutic antibody is selected from the group consisting of rituximab, herceptin, trastuzumab, alemtuzumab, bevacizumab, cetuximab and panitumumab, and
   (ii) at least one agent capable of reducing or preventing inhibitory signal transduction initiated via SIRPα, wherein said agent is an anti-CD47 antibody or an anti-SIRPα antibody or a Fab fragment, a F(ab')2 fragment or a scFv fragment thereof.

2. A method of enhancing in vivo efficacy of a therapeutic antibody to induce cancer cell destruction by ADCC in a subject receiving anti-cancer treatment with a therapeutic antibody comprising a human or non-human primate IgG Fc portion, wherein the therapeutic antibody induces antibody-dependent cellular cytotoxicity (ADCC), said method comprising administering to said subject prior to, simultaneously or after the administration of the therapeutic antibody, an agent capable of reducing or preventing inhibitory signal transduction initiated via SIRPα, wherein the agent is in an amount sufficient to increase ADCC such that the in vivo efficacy of the therapeutic antibody to induce cancer cell destruction by ADCC is enhanced, and wherein said agent is an anti-CD47 antibody or an anti-SIRPα antibody or a Fab fragment, a F(ab')2 fragment or a scFv fragment thereof.

* * * * *